United States Patent [19]

Walther et al.

[11] 4,313,931
[45] Feb. 2, 1982

[54] FUSED DIBENZO IMIDAZOLO COMPOUNDS, COMPOSITIONS AND USE

[75] Inventors: Gerhard Walther, Bingen; Claus S. Schneider, Ingelheim; Karl-Heinz Weber; Armin Fügner, both of Gau-Algesheim, all of Fed. Rep. of Germany

[73] Assignee: Boehringer Ingelheim KG, Ingelheim am Rhein, Fed. Rep. of Germany

[21] Appl. No.: 236,818

[22] Filed: Feb. 23, 1981

[30] Foreign Application Priority Data

Mar. 8, 1980 [DE] Fed. Rep. of Germany ....... 3008944

[51] Int. Cl.³ .................. A61K 31/535; A61K 31/415; C07D 487/04; C07D 498/04
[52] U.S. Cl. .................................. 424/45; 424/248.51; 424/248.57; 424/248.58; 424/248.4; 424/267; 424/273 R; 260/243.3; 260/244.4; 260/245.6
[58] Field of Search ............... 260/243.3, 244.4, 245.6; 424/248.51, 248.57, 248.58, 248.4, 267, 273 R, 45

[56] References Cited

U.S. PATENT DOCUMENTS 3,860,606 1/1975 van der Berg .................. 260/245.6

*Primary Examiner*—John M. Ford
*Assistant Examiner*—R. W. Ramsuer

*Attorney, Agent, or Firm*—Hammond & Littell, Weissenberger & Muserlian

[57] ABSTRACT

This invention relates to a compound of the formula

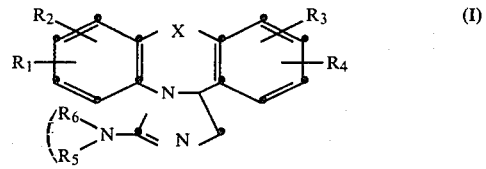

wherein
$R_1$, $R_2$, $R_3$, and $R_4$, which may be the same or different, each represent a hydrogen or halogen atom or an alkyl or alkoxy group of from 1 to 6 carbon atoms;
$R_5$ and $R_6$, which may be the same or different, each represent a hydrogen atom, an alkyl group of from 1 to 6 carbon atoms, or an alkenyl group of from 3 to 6 carbon atoms, or $R_5$ and $R_6$ together with the nitrogen atom to which they are attached represent a pyrrolidino, piperidino, or morpholino group; and
X represents oxygen, sulfur, or a methylene group,
or a non-toxic, pharmacologically acceptable acid addition salt thereof, or a racemate, enantiomer, or mixture of enantiomers thereof. The compounds of Formula I are useful in pharmaceutical compositions for treating bronchial asthma and allergic bronchitis.

6 Claims, No Drawings

FUSED DIBENZO IMIDAZOLO COMPOUNDS, COMPOSITIONS AND USE

FIELD OF THE INVENTION

This invention relates to novel heterocyclic compounds and acid addition salts thereof, to methods of preparing these compounds, to pharmaceutical compositions containing them as active ingredient, and to methods of using the pharmaceutical compositions.

More particularly, the present invention relates to a novel class of heterocyclic compounds represented by the formula

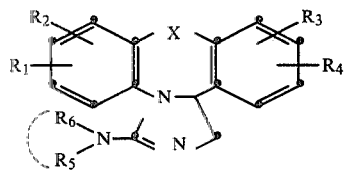

wherein
$R_1$, $R_2$, $R_3$, and $R_4$, which may be the same or different, each represent a hydrogen or halogen atom or an alkyl or alkoxy group of from 1 to 6 carbon atoms;
$R_5$ and $R_6$, which may be the same or different, each represent a hydrogen atom, an alkyl group of from 1 to 6 carbon atoms, or an alkenyl group of from 3 to 6 carbon atoms, or $R_5$ and $R_6$ together with the nitrogen atom to which they are attached represent a pyrrolidino, piperidino, or morpholino group; and
X represents oxygen, sulfur, or a methylene group, and the non-toxic, pharmacologically acceptable acid addition salts thereof.

The compounds of the invention can occur as racemates or as pure enantiomers, or as mixtures with various portions of the enantiomers, each in form of the free bases or the acid addition salts.

In the radicals $R_1$ to $R_6$, the alkyl, alkoxy, or alkenyl groups may be linear or branched. Consequently, the alkyl groups may comprise the following formulas:
—CH$_3$, —C$_2$H$_5$, —CH$_2$—CH$_2$—CH$_3$, —CH(CH$_3$)$_2$, —(CH$_2$)$_3$—CH$_3$, —CH$_2$—CH(CH$_3$)$_2$, —CH(CH$_3$)—C$_2$H$_5$, —C(CH$_3$)$_3$, —(CH$_2$)$_4$—CH$_3$, —CH$_2$—CH$_2$—CH(CH$_3$)$_2$, —CH$_2$—CH(CH$_3$)—C$_2$H$_5$, —CH(CH$_3$)—CH$_2$—CH$_2$—CH$_3$, —CH$_2$—C(CH$_3$)$_3$, —C(CH$_3$)$_2$—C$_2$H$_5$, —CH(CH$_3$)—CH(CH$_3$)$_2$, —(CH$_2$)$_5$—CH$_3$, —(CH$_2$)$_3$—CH(CH$_3$)$_2$, —CH$_2$—CH$_2$—CH(CH$_3$)—C$_2$H$_5$, —CH$_2$—CH(CH$_3$)—CH$_2$—CH$_2$—CH$_3$, —CH(CH$_3$)—(CH$_2$)$_3$—CH$_3$, —C(CH$_3$)$_2$—CH$_2$—CH$_2$—CH$_3$, —CH$_2$—C(CH$_3$)$_2$—C$_2$H$_5$, —CH$_2$—CH$_2$—C(CH$_3$)$_3$, —CH(CH$_3$)—CH(CH$_3$)—C$_2$H$_5$, —CH(CH$_3$)—CH$_2$—CH(CH$_3$)$_2$, —C(CH$_3$)$_2$—C(CH$_3$)$_2$, —CH(CH$_3$)—C(CH$_3$)$_3$, —CH$_2$—CH(C$_2$H$_5$)$_2$, —CH(C$_2$H$_5$)—(CH$_2$)$_2$—CH$_3$.

The alkoxy groups may contain the same carbon skeletons as the alkyl moiety therein.

As cyclic guanidine derivatives, the compounds of Formula I (if $R_6$ and optionally $R_5$ represent hydrogen) may occur also in their tautomeric form

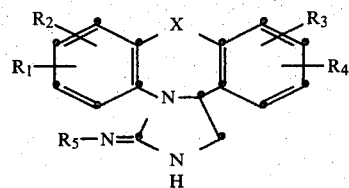

The designation of the positions of the compounds of Formula I and Ia is indicated in the following formula

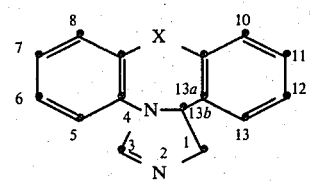

The compounds embraced by Formulas I and Ia may be prepared by the following methods:

Method A

A compound of the general formula

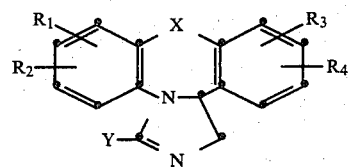

wherein
Y represents a halogen atom, for example, a chlorine atom, or an unsubstituted or substituted alkoxy or alkylthio group having from 1 to 8 carbon atoms in the alkyl moiety,
is reacted with an amine of the formula

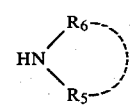

wherein $R_5$ and $R_6$ are as defined above. The reaction is effected in the melt or with the addition of conventional solvent (for example, an alcohol, ketone, ether, or aliphatic or aromatic hydrocarbon), optionally in an autoclave.

The amines of Formula III may serve as reaction medium as well. In general, the reaction is effected at temperatures up to the boiling temperature of the solvent employed.

The starting materials of Formula II may be obtained analogous to the methods known from the literature. Compounds where Y represents a halogen atom may be prepared by, for example, reaction of diamines of the formula

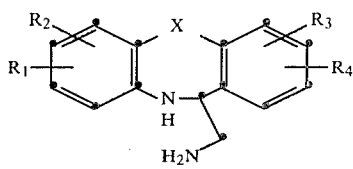

(IV)

with bifunctional carbonic acid derivatives such as phosgene, chlorocarbonic acid esters, or N,N′-carbonyldiimidazole to form the corresponding 3-oxo compounds of formula

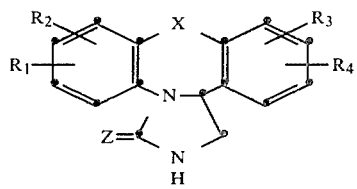

(V)

wherein Z represents oxygen, and subsequent halogenation of a corresponding inorganic acid chloride.

Compounds of Formula II where Y represents an alkylthio group are prepared by, for example, reacting the diamines of Formula IV with carbon disulfide, thiophosgene, or N,N′-thiocarbonyldiimidazole to form the corresponding 3-thioxo derivatives of Formula V where Z represents sulfur, which are subsequently alkylated with an alkyl halide to form the compounds of Formula II where Y represents an alkylthio group.

The diamines of Formula IV are obtained according to the reaction scheme:

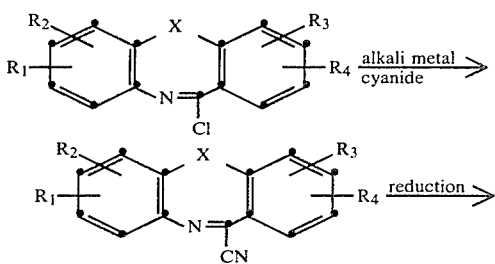

The compounds of Formula VI have been known [Lit. f.i. Helv. chim. Acta 49/II, 1433 ff (1966) or Helv. chim. Acta 50/I, 245 ff (1967)] or may be produced in accordance with a known procedure. The reaction of compounds of Formula VI with an alkali metal cyanide such as sodium cyanide is advantageously effected in DMSO at room temperature up to 60° C. Reduction of the cyano compounds of Formula VII is preferably effected with lithium aluminium hydride (LiAlH$_4$) or aluminum hydrogen (AlH$_3$) in tetrahydrofuran or diethylether, respectively.

Method B

A diamine of Formula IV is reacted with a cyanogen halogenide, such as cyanogen bromide, to form a compound of Formula I or Ia. The reaction is preferably effected at room temperature in an ethanol/tetrahydrofuran mixture. However, it can be effected as well in other solvents, such as an alcohol, chloroform, or a hydrocarbon such as toluene, xylene, or the like, optionally also with addition of a base such as, for example, potassium carbonate. The reaction temperatures are variable to a great extent and may rise up to the boiling temperature of the reaction mixture.

During reaction of the compound of Formula IV with, for example, cyanogen bromide, an intermediate compound of formula

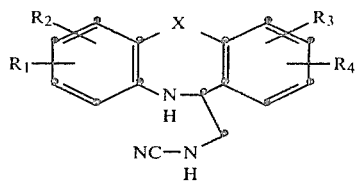

(IVa)

forms, which compound represents the proper starting material of the cyclization reaction. However, it is not necessary to isolate this compound as it continues reacting smoothly to the desired final product.

Method C

A compound of the formula

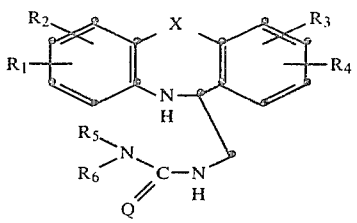

(VIII)

wherein
R$_1$ to R$_6$ are as defined above; and
Q represents oxygen, sulfur, or NR$_7$, where R$_7$ is an unsubstituted or substituted alkyl group of from 1 to 8 carbon atoms, such as, for example, a methyl, ethyl, propyl, or benzyl group is cyclized. Compounds of Formula VIII with Q=oxygen or sulfur, R$_5$=alkyl or alkenyl, and R$_6$=hydrogen can be obtained by reacting diamines of Formula IV with alkyl-isocyanates or alkenyl-isocyanates or with alkyl-isothiocyanates or alkenyl-isothiocyanates, respectively.

Cyclization to the compounds of Formula I or Ia according to the invention is effected by the action of acid halides, such as POCl$_3$, optionally in conventional solvents, such as toluene. A variant of this process consists of the S-alkylation of the thiourea derivatives of Formula VIII (Q=sulfur) to the corresponding alkylthio compounds of formula

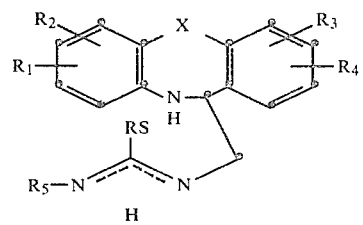

(IX)

wherein R represents an unsubstituted or substituted alkyl group with from 1 to 8 carbon atoms, which are cyclized in a known manner by heating in conventional solvents, such as, for example, alcohols or toluene, or in the melt to compounds of Formula I or Ia.

Compounds of Formula VIII with Q=NR₇ may be obtained by, for example, reacting diamines of Formula IV with correspondingly substituted or unsubstituted S-alkyl-isothiouureas. Cyclization to the compounds of Formula I or Ia is preferably carried out in the melt.

Method D

Diamines of Formula IV are reacted with N,N-disubstituted dichloromethylene-iminium salts of the formula

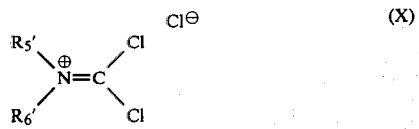

wherein $R_5'$ and $R_6'$ have the same meanings as $R_5$ and $R_6$ above, with the exception of hydrogen, to form compounds of Formula I, with the exception that neither $R_5$ nor $R_6$ represents hydrogen. The reaction is advantageously effected in an inert solvent, for example, chloroform, with the addition of a base, for example, triethylamine.

The reaction products obtained according to the various methods of preparation are isolated with the aid of known laboratory methods. If necessary, the raw products thus obtained may be purified using special methods, such as, for example, column chromatography, before they are crystallized in form of the bases or suitable salts.

If desired, racemates obtained according to the invention are separated into the enantiomers using conventional methods.

Free bases can be obtained from primarily obtained salts, and acid addition salts can be obtained from primarily obtained free bases, by use of conventional methods.

For the production of acid addition salts, acids suitable for the formation of therapeutically useful salts are especially used. Such acids include the following: hydrohalic acids such as hydrobromic acid, hydrochloric acid, hydroiodic acid, or hydrofluoric acid; aliphatic alicyclic, aromatic, or heterocyclic carboxylic acid or sulfonic acid, such as acetic acid, propionic acid, butyric acid, capronic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicyclic acid, ascorbic acid, methane-sulfonic acid, embonic acid, methanesulfonic acid, or toluenesulfonic acid, and acids such as nitric acid, sulfuric acid, phosphoric acid, or 8-chlorotheophylline or the like.

The novel compounds according to the invention are therapeutically useful or represent intermediate products for production of therapeutically useful compounds. While they enjoy a relatively low toxicity, they distinguish themselves by their long-lasting anti-allergic, anti-histaminic, and anti-serotonic activity. Furthermore, they inhibit the blood platelet aggregation. The novel compounds may be therapeutically used, for example, for the treatment of reactions provoked by liberation of histamine or serotonine, asthma bronchiale, allergic bronchitis, allergic rhinitis, allergic conjunctivitis, as well as allergic diathesis. The good oral effect of the compounds is of special significance for therapeutic purposes. It is also of essential advantage in comparison to the disodium salt of the cromoglycic acid, a widely used commercial product for the treatment of asthma bronchiale and allergic bronchitis.

The compounds according to the invention are processed for use with excipients and pharmaceutical carriers to prepare conventional galenic preparations in the conventional manner. Such conventional preparations include, for example, capsules, tablets, coated tablets, solutions, or suspensions for oral administration; aerosols for pulmonal administration; sterile isotonic aqueous solutions for parenteral administration; and creams, ointments, lotions, emulsions or sprays for local administration.

A single dose for oral administration to an adult is from about 0.2 to 40 mg (from about 0.0027 to 0.53 mg/kg of body weight), preferably from about 0.5 to 10 mg (from about 0.0067 to 0.13 mg/kg of body weight) of active ingredient. For inhalation, single doses of from about 0.5 to 20 mg (from about 0.0067 to 0.27 mg/kg of body weight), preferably from about 0.2 to 5 mg (from about 0.0027 to 0.067 mg/kg of body weight), are administered in conventional preparations, especially metering aerosols and capsules for powder inhalation. The indicates doses may optionally be administered several times per day.

To determine the effect of the compounds according to the invention, the compounds were subjected to numerous pharmacological tests:

(a) Tests in sensitized rats were performed after passive sensitization of the animals by IgE-antibodies and subsequent antigen challenge. In this manner a passive cutaneous anaphylaxis (GOOSE et al. (1969): Immunology 16, 749) (PCA) and a passive lung anaphylaxis (FARMER et al. (1975): Br. J. Pharmac. 55, 57) (PLA, experimental asthma) could be provoked.

(b) the anti-anaphylactic effect was confirmed in dogs per os, showing a hypersensitivity of the skin to ascaris antigen (BOOTH et al. (1970): J. Lab. clin. med. 76, 181).

(c) Anti-histaminic and anti-serotoninic activities:

The compounds inhibited p.o. and i.v. in rats, dogs, and monkeys, the reaction being induced by intracutaneous injection of histamine. Quantification was effected by measuring the reaction site after extravasation of Evans blue into the skin.

The anti-serotoninic effect was proved by the activity against the serotonine edema of the rat's paw (DOEPENER et al. (1958): Int. Arch. Allergy 12, 89).

The indications made in the following table are exemplary of the activities of the compounds according to the invention:

TABLE

| Compound | PCA ED$_{50}$ [mg/kg] (rat p.o.) | PLA ED$_{50}$ [mg/kg] (rat i.v.) | LD$_{50}$ [mg/kg] (mouse p.o.) |
| --- | --- | --- | --- |
| Example 1 | 6 | 0.052 | 325 |
| Example 1(a) | 0.96 | — | — |
| Example 1(c) | 1.1 | — | 340 |
| Example 1(d) | 2.5 | — | — |
| Example 1(i) | 3.8 | — | — |
| Example 1(l) | 5.4 | — | — |

The following examples are intended to illustrate the invention and should not be construed as limiting the invention thereto.

EXAMPLES

EXAMPLE 1

3-Amino-9,13b-dihydro-1H-dibenzo[c,f]imidazo[1,5-a]azepine hydrobromide

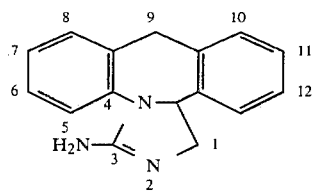

An amount of 6.72 g (0.03 mol) of 6-aminomethyl-6,11-dihydro-5H-dibenzo[b,e]azepine was dissolved in 60 ml of ethanol, and a solution of 3.18 g (0.03 mol) of bromo cyanogen in 25 ml of absolute tetrahydrofuran was added dropwise under stirring. The reaction mixture was stirred overnight at room temperature and then admixed with 50 ml of ether. Subsequently, resulting crystals were recovered by suction filtration.

Yield: 7.8 g (78.9% of theory); m.p.: 284°–286° C. (CH₃OH/ethylacetate).

The base liberated from the hydrobromide with aqueous sodium hydroxide solution had a melting point of 205°–208° C. (acetonitrile).

For the production of the hydrochloride, a suspension of the base in methanol was treated with the calculated quantity of etheric hydrochloric acid and, subsequently, the hydrochloride was precipitated under addition of ether. M.p.: 272°–273° C. (methanol/ether).

By use of procedures analogous to that described above, the following compounds were obtained:
(a) 3-amino-7-chloro-9,13b-dihydro-1H-dibenzo[c,f]-imidazo[1,5-a]azepine hydrochloride M.p.: 325°–329° C. (decomp.; alcohol)
(b) 3-amino-6-methyl-9,13b-dihydro-1H-dibenzo[c,f]-imidazo-1,5-a]azepine hydrobromide
(c) 3-amino-1,13b-dihydro-dibenzo[b,f]imidazo[1,5-d][1,4]-oxazepine hydrobromide

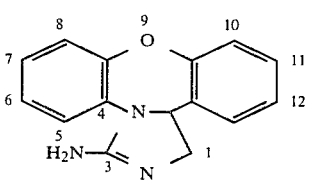

M.p.: 261°–264° C. (alcohol/ethylacetate)
(d) 3-amino-12-chloro-1,13b-dihydro[b,f]imidazo[1,5-d][1,4]oxazepine hydrobromide M.p.: 300° C. (acetonitrile/ethylacetate)
(e) 3-amino-7-chloro-1,13b-dihydro-bidenzo[b,f]imidazo[1,5-d][1,4]oxazepine hydrobromide M.p.: 297°–300° C. (alcohol/ether)
(f) 3-amino-6-chloro-1,13b-dihydro-dibenzo[b,f]imidazo[1,5-d][1,4]oxazepine hydrobromide M.p.: 282°–284° C. (methanol/ether)
(g) 3-amino-6-methyl-1,13b-dihydro-dibenzo[b,f]imidazo[1,5-d][1,4]oxazepine hydrobromide M.p.: 187°–189° C.
(h) 3-amino-12-methyl-1,13b-dihydro-dibenzo[b,f]imidazo[1,5-d][1,4]oxazepine hydrobromide M.p.: 309°–312° C.
(i) 3-amino-1,13b-dihydro-dibenzo[b,f]imidazo[1,5-d][1,4]-thiazepine hydrobromide

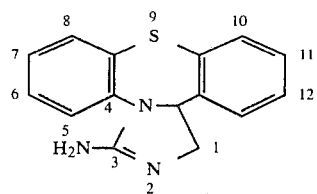

For production of the acid maleinate ($C_{15}H_{13}N_3S \times C_4H_4O_4$), the base liberated in the usual way was dissolved in methanol and admixed with the calculated quantity of maleic acid. The precipitated crystals were recrystallized from methanol under addition of charcoal (m.p.: 230° C. (decomp.))
(j) 3-amino-6-chloro-1,13b-dihydro-dibenzo[b,f]imidazo[1,5-d][1,4]thiazepine hydrobromide
(k) 3-amino-7-chloro-1,13b-dihydro-dibenzo[b,f]imidazo[1,5-d][1,4]thiazepine hydrobromide
(l) 3-amino-12-chloro-1,13b-dihydro-dibenzo[b,f]imidazo[1,5-d][1,4]thiazepine hydrobromide M.p.: 358°–361° C. (decomp.; methanol/ethylacetate)
(m) 3-amino-6-methyl-1,13b-dihydro-dibenzo[b,f]imidazo[1,5-d][1,4]thiazepine hydrobromide
(n) 3-amino-6-methoxy-1,13b-dihydro-dibenzo[b,f]imidazo[1,5-d][1,4]thiazepine hydrobromide

EXAMPLE 2

Preparation of a Diamine of Formula IV, 11-Aminomethyl-7-chloro-10,11-dihydro-dibenzo-[b,f][1,4]oxazepine fumarate

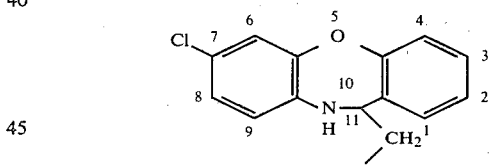

(A) 7-Chloro-11-cyano-dibenzo[b,f][1,4]oxazepine

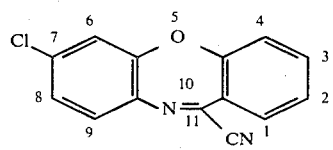

A suspension of 123 g (0.47 mol) of 7,11-dichloro-dibenz-[b,f][1,4]oxazepine and 46 g (0.94 mol) of sodium cyanide in 1400 ml of dimethylsulfoxide was stirred for 3 hours at 50°–60° C. The reaction mixture was cooled off and poured into 6 liters of ice water. The cooled reaction mixture was extracted with chloroform and, after drying with anhydrous sodium sulfate, the organic phase was evaporated in vacuo. The crystalline residue was washed with methanol and dried. The yield amounted to 74 g (62.4% of theory); m.p.: 185°–188° C.

The following cyano compounds were produced using analogous procedures:
(a) 8-chloro-11-cyano-dibenz[b,f][1,4]oxazepine Yield: 69.7% of theory; m.p.: 161°–168° C. (acetonitrile)
(b) 2-chloro-11-cyano-dibenz[b,f][1,4]oxazepine Yield: 31.4% of theory; m.p. of the raw product: 126°–132° C.
(c) 11-cyano-dibenzo[b,f][1,4]oxazepine Yield: 85.7% of theory; m.p. of the raw product: 107°–114° C.
(d) 11-cyano-dibenzo[b,f][1,4]thiazepine

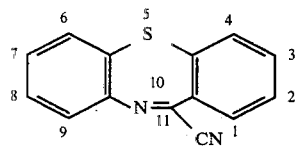

Yield: 100% of theory; m.p. of the raw product: 93°–100° C.
(e) 2-chloro-11-cyano-[b,f][1,4]thiazepine Yield: 65.3% of theory; m.p. of the raw product: 176°–182° C.
(f) 6-cyano-11-H-dibenz[b,e]azepine

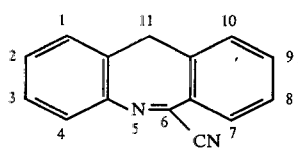

Yield: 73.2% of theory, m.p.: 98°–100° C. (methanol)
(g) 2-chloro-6-cyano-11H-dibenz[b,e]azepine Yield: 67.5% of theory; m.p. of the raw product: 163°–168° C.

(B) Reduction of 7-Chloro-11-cyano-dibenz[b,f][1,4]-oxazepine Obtained According to (A)

A solution of aluminum hydride in tetrahydrofuran was produced by slowly adding dropwise a solution of 9.8 g (0.1 mol) of 100% sulfuric acid in 40 ml of anhydrous tetrahydrofuran to a suspension of 7.6 g (0.2 mol) of lithium aluminum hydride in 200 ml of absolute tetrahydrofuran under stirring. Without separating the lithium sulfate that forms, there was added within 30 minutes a solution of 12.3 g (0.05 mol) of 7-chloro-11-cyano-dibenz[b,f][1,4]oxazepine in 80 ml of absolute tetrahydrofuran. The reaction mixture was stirred for 2 hours at room temperature and then was decomposed while ice-cooling the excess of the hydride by addition of 25 ml of water. The inorganic components were removed by suction filtration and stirred twice with chloroform. The tetrahydrofuran and the chloroform solutions were united, washed with an aqueous common salt solution, and, after drying with sodium sulfate, evaporated in vacuo. Twenty-five grams of a dark red oil remained as residue. For purification the oil was dissolved in methanol and converted with the calculated quantity of fumaric acid into the acid fumarate. Yield: 26 g (71.3% of theory); m.p.: 228° C. (decomp.)

The following diamines were produced using procedures analogous to that described in (B):
(a) 11-aminomethyl-8-chloro-10,11-dihydro-dibenzo[b,f][1,4]oxazepine fumarate Yield: 54.6% of theory; m.p. of the raw product: 239°–241° C. (decomp.)
(b) 11-aminomethyl-2-chloro-10,11-dihydro-dibenzo[b,f][1,4]oxazepine fumarate Yield: 54.4% of theory; m.p. of the raw product: 228°–229° C. (decomp.); m.p. of the base: 131°–133° C. (acetonitrile)
(c) 11-aminomethyl-10,11-dihydro-dibenz[b,f][1,4]oxazepine Yield: 65.5% of theory; m.p. of the base: 119°–122° C. (acetonitrile)
(d) 11-aminomethyl-10,11-dihydro-dibenzo[b,f][1,4]-thiazepine fumarate

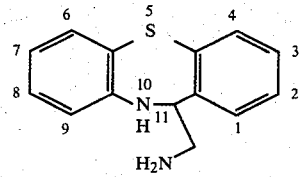

Yield: 61% of theory; m.p. of the raw product: 204°–206° C. (decomp.)
(e) 11-aminomethyl-2-chloro-10,11-dihydro-dibenzo[b,f][1,4]thiazepine fumarate Yield: 68.8% of theory; m.p. of the raw product: 202° C. (decomp.)
(f) 6-aminomethyl-6,11-dihydro-5H-dibenz[b,e]azepine fumarate

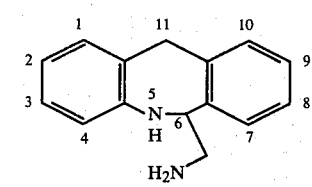

Yield: 72.3% of theory; m.p. of raw product: 192°–193° C. (decomp.)
(g) 6-aminomethyl-2-chloro-6,11-dihydro-5H-dibenz[b,e]azepine fumarate Yield: 42.1% of theory; m.p. of crude product: 197°–198° C. (decomp.)

EXAMPLE 3

3-Morpholino-1,13b-dihydro-dibenz[b,f]imidazo[1,5-d][1,4]oxazepine fumarate (A)

3-Methylmercapto-1,13b-dihydro-dibenz[b,f]imidazo[1,5-d][1,4]oxazepine hydroiodide Twenty grams (0.075 mol) of 1,2,3,13b-tetrahydro-dibenz[b,f]imidazo[1,5-d][1,4]oxazepine-3-thione (m.p. 199°–201° C.; made of 11-aminomethyl-10,11-dihydro-dibenz[b,f][1,4]-oxazepine and carbon disulfide) were admixed with a solution of 21.4 g (0.15 mol) of methyliodide in 170 ml of methanol and refluxed for three hours. In doing so, a clear solution was primarily obtained, out of which crystals gradually separated. After cooling, the precipitate was removed by suction filtration and dried. Crude yield: 26.6 g (87% of theory); m.p.: 219°–228° C. (decomp.).

In analogous manner, the 3-methylmercapto-9,13b-dihydro-1H-dibenz[c,f]imidazo[1,5-a]azepine hydroiodide (m.p. of the raw product: 274°–283° C. (decomp.)) was obtained from 6-aminomethyl-6,11-dihydro-5H-dibenz[b,e]azepine via 2,3,9,13b-tetrahydro-1H-dibenz[c,f]imidazo[1,5-a]azepine-3-thione (m.p.: 222°–224° C.).

The 3-methylmercapto derivatives can be reacted without further purification.

(B) An amount of 8.2 g (0.02 mol) of 3-methylmercapto-1,13b-dihydro-dibenz[b,f]imidazo[1,5-d][1,4]oxazepine hydroiodide was refluxed with 25 ml of morpholine for two hours under stirring. The resulting light-yellow solution was evaporated in vacuo, and the residue was distributed between ether and 2 N sodium hydroxide solution. Subsequently, the organic phase was washed with water, dried with sodium sulfate, and evaporated. The residue was recrystallized from acetonitrile (m.p.: 141°–142° C.). For production of the acid fumarate, the base thus obtained was dissolved in alcohol and admixed with the calculated quantity of fumaric acid. During cooling, there were obtained 5.8 g (66.4% of theory) of 3-morpholino-1,13b-dihydro-dibenz[b,f]imidazo[1,5-d][1,4]oxazepine hydrogen fumarate, m.p.: 189°–191° C. (decomp.).

By use of procedures analogous to that set forth in (B), the following compounds were prepared from the corresponding methylmercapto compounds:

(a) 3-n-pentylamino-9,13b-dihydro-1H-dibenz[c,f]imidazo[1,5-a]azepine, which was converted into the hydrochloride in the usual way. M.p. of hydrochloride: 192°–195° C.

(b) 3-morpholine-9,13b-dihydro-1H-dibenz[c,f]imidazo[1,5-a]azepine hydrochloride M.p.: 204°–207° C. (decomp.)

EXAMPLE 4

3-Allylamino-9,13b-dihydro-dibenz[b,f]imidazo[1,5-d][1,4]oxazepine hydrochloride An amount of 8.2 g (0.02 mol) of 3-methylmercapto-1,13b-dihydro-dibenz[b,f]imidazo[1,5-d][1,4]oxazepine hydroiodide was heated with 3.42 g (0.06 mol) of allylamine for two hours to 70° C. under stirring. After cooling the light-yellow oil was admixed with 2 N sodium hydroxide solution and was subsequently extracted with ether. The organic phase was separated, washed with water, and dried over anhydrous sodium sulfate. Evaporation in vacuo resulted in 5.6 g of raw base, which was converted in the conventional way with methanolic hydrochloric acid into the hydrochloride. Yield: 4.1 g (62.6% of theory) M.p.: 189°–192° C. (acetonitrile)

EXAMPLE 5

3-Dimethylamino-1,13b-dihydro-dibenz[b,f]imidazo[1,5-d][1,4]oxazepine hydrochloride Three grams (7.4 mmol) of 3-methylmercapto-1,13b-dihydrodibenz[b,f]imidazo[1,5-d][1,4]oxazepine hydroiodide were heated to 130° C. in an autoclave with a solution of 15 ml of dimethylamine in 30 ml of ethanol for three hours. The resin remaining after evaporation of the reaction solution was taken up in chloroform and shaken out with 2 N sodium hydroxide solution. The organic phase was dried with sodium sulfate, and the solvent was distilled off in vacuo. An amount of 2.6 g of oil (crude base) was obtained, which was converted with methanolic hydrochloric acid into the hydrochloride (m.p.: 163°–167° C.; acetonitrile/ether). The substance contained 1 mol of water (Karl Fischer titration).

Using procedures analogous to that described above, the following compounds were prepared from the corresponding methylmercapto derivatives.

(a) 3-dimethylamino-9,13-dihydro-1H-dibenz[c,f]imidazo[1,5-a]azepine hydrochloride; m.p.: 268°–271° C.

(b) 3-dimethylamino-1,13b-dihydro-dibenz[b,f]imidazo[1,5-d][1,4]thiazepine hydrochloride; m.p.: 241°–244° C.; the substance contained 0.5 mol of water.

Under similar reaction conditions the following compounds were obtained by reacting 3-methylmercapto-9,11b-dihydro-1H-dibenz[c,f]imidazo[1,5-a]azepine hydroiodide with alcoholic solutions of ammonia or the respective corresponding amines:

(c) 3-amino-9,13b-dihydro-1H-dibenz[c,f]imidazo[1,5-a]azepine hydrochloride (m.p.: 283°–286° C.). (This substance was identical to the product obtained according to Example 1.)

(d) 3-pyrrolidino-9,13b-dihydro-1H-dibenz[c,f]imidazo[1,5-a]azepine hydrochloride; m.p.: 158°–162° C. (decomp.; alcohol/ether). This substance contained 0.25 mol of water.

(e) 3-methylamino-9,13b-dihydro-1H-dibenz[c,f]imidazo[1,5-a]azepine hydrochloride; m.p.; 234° C. (decomp.; methanol/ether).

(f) 3-ethylamino-9,13b-dihydro-1H-dibenz[c,f]imidazo[1,5-a]azepine hydrochloride; m.p.: 275°–280° C.

(g) 3-allylamino-1,13b-dihydro-1H-dibenz[c,f]imidazo[1,5-a]azepine hydrochloride; m.p.: 202°–205° C. (acetonitrile/ethylacetate).

EXAMPLE 6

3-Dimethylamino-7-chloro-9,13b-dihydro-1H-dibenz[c,f]imidazo[1,5-a]azepine hydrochloride An amount of 4.21 g (0.026 mol) of dichloromethylene dimethylammonium chloride was added dropwise to a solution of 6.7 g (0.026 mol) of 6-aminomethyl-2-chloro-6,11-dihydro-5H-dibenz[b,e]azepine and 5.76 g (0.057 mol) of triethylamine in 70 ml of chloroform, under stirring. In so doing, a slightly exothermic reaction occurred. The reaction solution was refluxed for another hour, cooled off, and shaken out successively with 2 N hydrochloric acid and 2 N sodium hydroxide solution. The organic phase was washed with water, dried over anhydrous sodium sulphate, and evaporated in vacuo. Subsequently the residue was chromatographed on silica gel. Then, impurities were separated with acetone and methanol, and the desired product was eluted with a mixture of chloroform/methanol/conc. $NH_3$ (65/35/1). After evaporation of the chloroform/methanol/conc. $NH_3$ eluates, 4.5 g of oil were obtained. This raw base was dissolved in ether and, after filtration to remove insoluble particles, converted with methanolic hydrochloric acid into the hydrochloride. Yield: 3.7 g (40% of theory); m.p.: 195°–197° C. (decomposition from acetonitrile/ethylacetate). The substance contained 0.5 mol of water.

EXAMPLE 7

3-Methylamino-6-chloro-9,13b-dihydro-dibenz[b,f]imidazo[1,5-d][1,4]oxazepine-hydrochloride (A) A solution of 9.2 g (0.035 mol) of 11-aminomethyl-8-chloro-10,11-dihydro-dibenz[b,f][1,4]oxazepine and 2.58 g (0.035 mol) of methylisothiocyanate was stirred for two hours at room temperature and subsequently allowed to rest overnight. After evaporation of the reaction solution, a crystalline residue of 11.7 g (m.p.: 126°–132° C.) was obtained.

(B) Ten grams (0.03 mol) of the thio-urea derivatives obtained in (A) were dissolved in a methanolic solution of 6.38 g (0.045 mol) of methyl iodide in 80 ml of methanol, and the reaction mixture was subsequently refluxed for two hours. The resulting precipitate, N-{8-chloro- 10,11-dihydrodibenz[b,f][1,4]oxazepine-11-yl}methyl-S-methyl-thio-urea hydroiodide (melting point: 212°–215° C.), was removed by suction filtration and dried.

(C) To liberate the base, a suspension of 9.7 g of the hydroiodide obtained according to (B) in water was admixed with 2 N sodium hydroxide solution and ether and was stirred until there were 2 clear layers. The organic phase was separated, dried with anhydrous sodium sulphate, and evaporated in vacuo. The residue of 7.1 g (0.02 mol of base) was dissolved in 60 ml of xylene, and the solution was refluxed for 11 hours. The crystals precipitating when the reaction solution cooled off (5.6 g) were removed by suction filtration, dissolved in methanol, and converted with etheric hydrochloric acid into the hydrochloride. For further purification the salt was taken up in dilute sodium acetate solution. The resulting aqueous solution was shaken out with ether, adjusted alkaline with sodium hydroxide solution, and extracted subsequently with chloroform. The organic phase was dried with anhydrous sodium sulphate and evaporated in vacuo. The remaining base was converted into the hydrochloride. Yield: 4.1 g (61% of theory); m.p.: 297°–300° C. (CH₃OH/ether).

EXAMPLE 8

Using procedures analogous to those of Example 7, N-{10,11-dihydro-dibenz[b,f][1,4]oxazepine-11-yl}-methyl-S-methylthio-urea hydroiodide was prepared, with 11-aminomethyl-10,11-dihydro-dibenz[b,f][1,4]oxazepine being employed as starting material. The base liberated therefrom was reacted to form 3-methylamino-9,13b-dihydro-dibenz[b,f]imidazo[1,5-d][1,4]oxazepine by heating the base for three hours in toluene, with splitting of methylmercaptan. The hydrochloride had a melting point of 328°–330° C. (decomposition).

EXAMPLE 9

3-Methylamino-7-chloro-9,13b-dihydro-dibenz[b,f]imidazo[1,5-d][1,4]oxazepine hydrochloride (A)
N-{7-chloro-10,11-dihydro-dibenz[b,f][1,4]oxazepine-11-yl}-N-methyl-urea A solution of 2.68 (0.045 mol) of methylisocyanate in 40 ml of toluene was added dropwise to a solution of 11 g (0.042 mol) of 11-aminomethyl-7-chloro-10,11-dihydro-dibenz[b,f][1,4]oxazepine in 60 ml of toluene. After a reaction time of two hours, the precipitated crystals were removed by suction filtration and dried. Yield: 10.8 g (80.5% of theory); m.p.: 146°–149° C.

(B) A suspension of 10.8 g (0.034 mol) of the urea derivative produced according to (A) in 200 ml of toluene was admixed with 10.8 ml of phosphorus oxychloride, and the reaction mixture was refluxed for 30 minutes. After evaporation of the solvent, the residue was distributed between cold, dilute sodium hydroxide solution and chloroform. The organic phase was dried over anhydrous sodium sulphate and evaporated in vacuo. Yield: 6.2 g (60.9% of theory); m.p.: 163°–165° C. (acetonitrile). The hydrochloride produced in the conventional way had a melting point of 298°–302° C. (CH₃OH/ethylacetate).

EXAMPLE 10

In accordance with the procedures set forth in Example 9, a solution containing isopropylisocyanate was added dropwise to a solution containing 6-aminomethyl-6,11-dihydro-5H-dibenz[b,e]azepine to form a corresponding urea derivative (m.p.: 190°–192° C.), and then the urea derivative was converted to 3-isopropylamino-9,13b-dihydro-1H-dibenz[c,f]imidazo[1,5-a]azepine. The hydrochloride melted at 241°–243° C. (decomposition).

EXAMPLE 11

(−)3-amino-9,13b-dihydro-1H-dibenz[c,f]imidazo[1,5-a]azepine hydrochloride and
(+)3-amino-9,13b-dihydro-1H-dibenz[c,f]imidazo[1,5-a]azepine hydrochloride An amount of 36.5 g (0.146 mol) of racemic 3-amino-9,13b-dihydro-dibenz[c,f]imidazo[1,5-a]azepine base and 55.1 g (0.164 mol) of dibenzoyl-L(+)-tartaric acid were dissolved hot in a liter of methanol. The solution was allowed to cool off, during which crystals precipitated. After the solution and crystals were allowed to stand for a while, that is, for a few hours, the crystals were removed by suction filtration. The crystals were recrystallized from methanol to provide crystals having a constant melting point, 150°–152° C. (decomp.), and a specification rotation, $[\alpha]_D^{25}$: −200° (c=1; methanol).

The base liberated in the conventional way was dissolved in methanol and converted into the hydrochloride with etheric hydrochloric acid. M.p.: 266°–269° C.; $[\alpha]_D^{25}$: −285° (c=1; alcohol).

In analogous manner the (+)enantiomer was obtained using dibenzoyl-D(−)-tartaric acid. Hydrochloride: m.p.: 266°–269° C.; $[\alpha]_D^{25}$: +285° (c=1; alcohol).

The following examples illustrate a few pharmaceutical dosage unit compositions comprising a compound of Formula I, or an acid addition salt thereof, as active ingredient.

EXAMPLE 12

Tablets

Composition of one tablet:

| Component | Amount |
|---|---|
| Active ingredient | 0.005 g |
| Stearic acid | 0.001 g |
| Glucose | 0.194 g |
| | 0.200 g |

The active ingredient and the stearic acid are intimately admixed with each other, the resulting mixture is granulated by moistening it with water and passing the moist mass through a screen, and granulate is dried and then intimately admixed with the glucose. The resulting composition is compressed into 200 mg-tablets, each of which is an oral dosage composition containing 5 mg of active ingredient.

EXAMPLE 13

Inhalation Aerosol

Composition of aerosol:

| Component | Amount |
|---|---|
| Active ingredient | 1.00 |
| Soy lecithin | 0.20 |
| Propellant gas mixture (Frigen 11, 12, and 14) | |

-continued

| Component | Amount |
|---|---|
| q.s. ad | 100.00 |

The preparation is preferably filled into aerosol containers with metering valves, the single stroke being adjusted to release a dose of 0.5 mg. For the other dosage-units within the indicated range, it is useful to apply preparations with a higher or lower portion of active ingredient.

EXAMPLE 14

Capsules for Inhalation

The active ingredient according to Formula I is filled in micronized form (particle size mostly between 2 and 6 μm), optionally with addition of micronized carriers, such as, for example, lactose, into hard gelatin capsules. Each capsule is filled with, for example, from about 0.2 to 20 mg of active substance and from about 0 to 40 mg of lactose. Conventional powder inhalation devices are used for inhalation.

EXAMPLE 15

Ointment

Composition of 100 g of ointment:

| Component | Amount |
|---|---|
| Active ingredient | 2.000 g |
| Fuming hydrochloric acid | 0.011 g |
| Sodium pyrosulfite | 0.050 g |
| Mixture of cetyl alcohol and stearyl alcohol (1:1) | 20.000 g |
| White vaseline | 5.000 g |
| Artificial bergamot oil | 0.075 g |
| Distilled water    q.s. ad | 100.000 g |

The components are worked up to an ointment in the conventional way.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

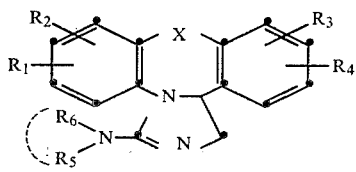

wherein
 $R_1$, $R_2$, $R_3$, and $R_4$, which may be the same or different, each represent a hydrogen or halogen atom or an alkyl or alkoxy group of from 1 to 6 carbon atoms;
 $R_5$ and $R_6$, which may be the same or different, each represent a hydrogen atom, an alkyl group of from 1 to 6 carbon atoms, or an alkenyl group of from 3 to 6 carbon atoms, or $R_5$ and $R_6$ together with the nitrogen atom to which they are attached represent a pyrrolidino, piperidino, or morpholino group; and
 X represents oxygen, sulfur, or a methylene group, or a non-toxic, pharmacologically acceptable acid addition salt thereof, or a racemate, enantiomer, or mixture of enantiomers thereof.

2. The compound of claim 1, wherein $R_5$ and $R_6$ each represent a hydrogen atom.

3. A pharmaceutical dosage unit composition consisting essentially of an inert pharmaceutical carrier and an effective amount of a composition of claim 1.

4. A method of treating reactions provoked by liberation of histamine or serotonine; bronchial asthma; allergic bronchitis; allergic rhinitis; allergic conjunctivitis; or allergic diathesis in a warm-blooded host, which comprises administering to said host an effective amount of a compound of claim 1.

5. The method of claim 4 for treating bronchial asthma.

6. The method of claim 4 for treating allergic bronchitis.

* * * * *

UNITED STATES PATENT AND TRADEMARK OFFICE
CERTIFICATE OF CORRECTION

PATENT NO. : 4,313,931  
DATED : February 2, 1982  
INVENTOR(S) : GERHARD WALTHER ET AL.

It is certified that error appears in the above—identified patent and that said Letters Patent is hereby corrected as shown below:

Column 1, lines 47, 58 and 60: "CH(CH-" should be -- $CH(CH_3)-$ --.

Column 1, lines 48, 59 and 61: Delete "$_3)-$".

Column 1, lines 49 and 53: "-CH-" should be -- $-CH_2-$ --.

Column 1, lines 50, 54 and 60: Delete "$_2-$".

Column 1, line 54: "$-CH_2-CH(CH-$" should be -- $-CH_2-CH(CH_3)-$ --.

Column 1, line 56: "$-CH_2-C(CH_3-$" should be -- $-CH_2-C)CH_3)_2-$ --.

Column 1, line 57: Delete "$)_2-$".

Column 1, line 59: "$-CH(CH_3)-CH-$" should be -- $-CH(CH_3)-CH_2-$ --.

Column 1, line 61: "$-CH(C_2H-$" should be -- $-CH(C_2H_5)-$ --.

Column 1, line 62: Delete "$_5)-$".

Column 10, line 35: "dibenz[-" should be -- dibenz- --.

UNITED STATES PATENT AND TRADEMARK OFFICE
CERTIFICATE OF CORRECTION

PATENT NO. : 4,313,931
DATED : February 2, 1982
INVENTOR(S) : GERHARD WALTHER ET AL.

It is certified that error appears in the above—identified patent and that said Letters Patent is hereby corrected as shown below:

Column 10, line 36: "b,e]" should be -- [b,e] --.

Column 10, line 50: "methyli-" should be -- methyl- --.

Column 10, line 51; Column 11, line 49: "odide" should be -- iodide --.

Column 11, line 48: "hydroi-" should be -- hydro- --.

Signed and Sealed this

Eighteenth Day of May 1982

[SEAL]

Attest:

GERALD J. MOSSINGHOFF

Attesting Officer

Commissioner of Patents and Trademarks